(12) United States Patent
Waatti

(10) Patent No.: US 7,399,418 B2
(45) Date of Patent: Jul. 15, 2008

(54) FORMULATION AND METHOD FOR CHLORINATING RECREATIONAL WATER

(75) Inventor: Kurt John Waatti, Crystal Lake, IL (US)

(73) Assignee: Rohm and Hass Company, Philadelphia, PA (US)

( * ) Notice: Subject to any disclaimer, the term of this patent is extended or adjusted under 35 U.S.C. 154(b) by 0 days.

(21) Appl. No.: 11/585,700

(22) Filed: Oct. 24, 2006

(65) Prior Publication Data

US 2008/0093305 A1 Apr. 24, 2008

(51) Int. Cl.
*C11D 3/00* (2006.01)

(52) U.S. Cl. ..................................... 210/748

(58) Field of Classification Search .............. 210/748, 210/600; 510/438; 260/248; 252/187 C
See application file for complete search history.

(56) References Cited

U.S. PATENT DOCUMENTS

| 4,594,091 A | | 6/1986 | Girvan |
| 5,478,482 A | | 12/1995 | Jones et al. |
| 5,567,283 A | | 10/1996 | Lynn et al. |
| 5,676,844 A | * | 10/1997 | Girvan ................. 210/756 |
| 5,698,506 A | * | 12/1997 | Angevaare et al. ........ 510/222 |
| 6,207,177 B1 | | 3/2001 | Jany |
| 7,238,287 B2 | * | 7/2007 | Kulperger ............... 210/632 |
| 2005/0079990 A1 | * | 4/2005 | Chan et al. ............... 510/438 |
| 2006/0054569 A1 | * | 3/2006 | Kulperger ............... 210/755 |

FOREIGN PATENT DOCUMENTS

| EP | 555598 | 8/1996 |
| EP | 1178016 | 2/2002 |
| WO | WO 2005/051850 | 6/2005 |

* cited by examiner

*Primary Examiner*—Walter D. Griffin
*Assistant Examiner*—Cameron J Allen
(74) *Attorney, Agent, or Firm*—Kenneth Crimaldi

(57) ABSTRACT

A solid composition comprising: (a) a sodium or potassium salt of cyanuric acid; and (b) a mixture of a tetraborate salt and boric acid in amounts sufficient to produce a pH from 7 to 8. Optionally, the composition further comprises sodium chloride or potassium chloride.

15 Claims, No Drawings

FORMULATION AND METHOD FOR CHLORINATING RECREATIONAL WATER

BACKGROUND

This invention relates generally to a formulation useful in a body of recreational water equipped with a chlorine generator, and to a method useful in chlorinating water for recreational purposes.

Electrolytic chlorine generators are used to produce chlorine in the form of hypochlorite from chloride ion present in recreational water, e.g., water used in pools, spas, hot tubs, etc., for the purposes of sanitation and oxidation. For maximum chlorine effectiveness and stability, pH is maintained in the range from 7-8. For example, U.S. Pat. No. 5,478,482 teaches the use of a borate buffer system to achieve pH control in a chlorinated aqueous system. However, this reference does not provide control of other problems encountered in these systems.

The problem addressed by this invention is to provide an improved formulation for treating recreational water.

STATEMENT OF INVENTION

The present invention is directed to a solid composition comprising: (a) a potassium or sodium salt of cyanuric acid having a pH from 5.8 to 7.3; and (b) a mixture of a tetraborate salt and boric acid in amounts sufficient to produce a pH from 7 to 8. Optionally, the solid composition further comprises sodium or potassium chloride.

The present invention further comprises a method for providing chlorinated water for recreational purposes by adding solids comprising: (a) a sodium or potassium salt of cyanuric acid having a pH from 5.8 to 7.3; (b) a tetraborate salt and boric acid in amounts sufficient to produce a pH from 7 to 8; and (c) sodium chloride or potassium chloride; to a body of recreational water equipped with a chlorine generator, followed by electrolysis of the treated water to produce chlorine.

DETAILED DESCRIPTION

All percentages and ratios are by weight, unless otherwise indicated. Concentrations in parts per million ("ppm") are calculated on a weight/weight basis.

The composition of this invention contains a sodium or potassium salt of cyanuric acid. Preferably, the composition is made from a sodium or potassium salt of cyanuric acid having a pH from 5.8 to 7.3. This "salt" is a mixture produced from partial neutralization of cyanuric acid, and thus the mixture contains some cyanuric acid as well as at least one cyanuric acid salt. Preferably, the cyanuric acid salt is a sodium salt. The pH is measured at room temperature for a solution produced by dissolving 0.23 g of the cyanuric acid salt in 3 L of deionized water. Preferably, the pH is from 6 to 7.2, more preferably from 6.2 to 7. The sodium or potassium salt is believed to contain a mixture of cyanuric acid, mono-sodium or mono-potassium cyanurate, di-sodium or di-potassium cyanurate and tri-sodium or tri-potassium cyanurate, although the amounts of di- and tri-sodium or potassium cyanurates are believed to be very small. The relative amounts will vary somewhat depending on the pH. The majority of the salt of cyanuric acid is believed to be a mixture of cyanuric acid and mono-sodium or mono-potassium cyanurate, comprising at least 95% of the mixture, on a dry basis. Cyanuric acid sodium salts useful in this invention typically have from 7% Na to 10% Na, preferably from 7.8% Na to 9% Na, and more preferably from 8.1% Na to 8.7% Na, on an "as is" basis (the sodium salt is a monohydrate). Cyanuric acid potassium salts useful in this invention typically have amounts of potassium corresponding to the same degree of neutralization as those given above for sodium, i.e., from 10.9% K to 15.5% K, preferably from 12% K to 14% K, and more preferably from 12.6% K to 13.5% K. The pH of the cyanuric acid salt used in the formulation is extremely important in controlling the pH of an aqueous solution of the overall composition, and in improving dissolution rate of the cyanuric acid salt. If the pH of the cyanuric acid salt is too high, excessive amounts of pH buffering agents are required to control the pH of the formulation, and the dissolution rate of the salt tends to be slower. Low-pH salts also have longer dissolution times. When the composition of this invention also contains sodium or potassium chloride, preferably, the amount of the cyanuric acid salt, as the monohydrate, in the composition is from 1% to 3.5%, more preferably from 1.5% to 3%, and most preferably from 2% to 2.8%. When the composition does not contain sodium or potassium chloride, preferably the amount is from 20% to 60%, more preferably from 30% to 55%, and most preferably from 38% to 50%. In one embodiment of the invention, the sodium or potassium salt of cyanuric acid is produced by forming an aqueous slurry of cyanuric acid and NaOH or KOH, heating the slurry, and then cooling to precipitate a mixture of sodium or potassium cyanurate and cyanuric acid. Preferably, the slurry is heated to at least 30° C., more preferably to at least 50° C., and most preferably at about 60-80° C.; preferably the temperature is no more than 100° C. Preferably, the slurry contains at least 200 g cyanuric acid/L water, more preferably at least 500 g cyanuric acid/L water; preferably there is no more than 1000 g cyanuric acid/L water.

A tetraborate salt and boric acid are present in the composition of this invention as an effective pH buffer system. Suitable tetraborate salts include, e.g., sodium, potassium, lithium and ammonium. Sodium tetraborate and potassium tetraborate are preferred; and sodium tetraborate is especially preferred. Preferably, amounts of the tetraborate salt and boric acid in the composition are balanced to provide a pH from 7.2 to 7.8 in the recreational water, preferably at a concentration in water of 3000 to 3500 ppm of the formulation, including sodium or potassium chloride. A convenient and available form of sodium tetraborate is sodium tetraborate pentahydrate. Preferably, the ratio of boric acid to sodium tetraborate pentahydrate is from 1.5:1 to 4:1, more preferably from 2.5:1 to 3:1. When the composition of this invention also contains sodium or potassium chloride, preferably, the total amount of the pH buffer system is from 1.5% to 4% of the composition, more preferably from 2% to 3.5%, and most preferably from 2.5% to 3.5%. When the composition does not contain sodium or potassium chloride, preferably the amount of pH buffer is from 30% to 70%, more preferably from 40% to 62%, and most preferably from 45% to 62%.

In one embodiment of the invention, a metal chelating agent is present in the composition to control scale and staining by metal ions. Preferably, the metal chelating agent is a chelating aminocarboxylic acid. A chelating aminocarboxylic acid is a compound having an amine group, and having at least two carboxylic acid groups that can form coordinate bonds to a single metal atom. Preferred chelating aminocarboxylic acids useful in the present invention include, e.g., ethylenediaminetetraacetic acid (EDTA), hydroxyethylethylenediaminetriacetic acid, nitrilotriacetic acid (NTA), N-dihydroxyethylglycine and ethylenebishydroxyphenyglycine. Particularly preferred chelating aminocarboxylic acids are EDTA and NTA, and EDTA is most preferred. When the composition of this invention also contains sodium or potassium chloride, preferably, the amount of metal chelating agent in the composition is from 0.1% to 0.4%, more preferably from 0.15% to 0.3%, and most preferably from 0.2% to 0.25%. When the composition does not contain sodium or potassium chloride, preferably the amount is from 2% to 8%, more preferably from 3% to 6%, and most preferably from 3.5% to 4.5%.

In one embodiment of the invention, the composition also contains sodium chloride or potassium chloride. Preferably, the amount of sodium chloride or potassium chloride is from 93% to 97%. More preferably, the amount of sodium chloride or potassium chloride is from 94% to 96%, and most preferably from 94% to 95%. Preferably, the composition is added to water in an amount from 1000 ppm to 5000 ppm, more preferably from 2000 ppm to 4000 ppm, and most preferably from 2600 ppm to 3800 ppm. Preferably, the composition contains sodium chloride. In the method of this invention, the components may be added to the recreational water separately, or combined, partially or completely, prior to addition. In one embodiment, sodium or potassium chloride is added to water separately from the other ingredients, all of which were combined prior to addition to water.

EXAMPLE 1

Stability of Cyanuric Acid/Sodium Chloride vs. Pool Salt Composition

Five gallons of balanced pool water was prepared by adding the appropriate quantities of $CaCl_2$ and $NaHCO_3$ to a concentration of 326 mg/L calcium and 116 mg/L bicarbonate.

For the testing, 1000 mL of balanced water was added to 2-1500 mL beakers. To each beaker, 3.2 g of common granulated salt (Morton PUREX® salt) was added to give a salt concentration of approximately 3,200 ppm. For the Control beaker, 0.06 g of cyanuric acid was dissolved into the balanced pool water to give a concentration of approximately 60 mg/L (ppm). The initial pH of 7.16 was adjusted to 7.5 with NaOH. For the Pool Salt test, 0.19 g of a premix containing sodium cyanurate/cyanuric acid mixture (0.0818 g, 42.48%, pH=6.62, 8.3% Na), boric acid (0.0734 g, 38.94%), sodium tetraborate pentahydrate (0.0282 g, 14.51%) and EDTA (0.0087 g, 4.07%) was added to the water {concentrations for premix+sodium chloride: sodium chloride (94.4%), sodium cyanurate/cyanuric acid mixture (2.38%), boric acid (2.18%), sodium tetraborate pentahydrate (0.81%) and EDTA (0.23%) }. The initial pH of 7.58 was adjusted to 7.5 with dilute HCl. Each solution was titrated with 0.05 N NaOH and pH was recorded after each incremental addition. The solutions were titrated with base until $CaCO_3$ began to precipitate and they turned cloudy. The results of this test are shown in Table I.

TABLE I

Titration Curves

| Control | | Pool Salt Formula | |
|---|---|---|---|
| mL 0.05 N NaOH | pH | mL 0.05 N NaOH | pH |
| 0.00 | 7.5 | 0.00 | 7.50 |
| 2.00 | 7.98 | 5.00 | 8.04 |
| 4.00 | 8.45 | 10.00 | 8.41 |
| 6.00 | 8.78 | 15.00 | 8.66 |
| 8.00 | 9.02 | 20.00 | 8.87 |
| 10.00 | 9.20 | 25.00 | 9.04 |
| 11.00 | 9.27 | 30.00 | 9.18 |
| 11.25 | 9.28 | 31.00 | 9.22 |

TABLE I-continued

Titration Curves

| Control | | Pool Salt Formula | |
|---|---|---|---|
| mL 0.05 N NaOH | pH | mL 0.05 N NaOH | pH |
| Solution turned cloudy and pH began to drop. No more base was added. | | Solution turned cloudy and pH began to drop. No more base was added | |
| 3 minutes | 8.73 | 3 minutes | 9.08 |
| 25 minutes | 8.35 | 45 minutes | 8.56 |

The results demonstrate that nearly 3 times much base was required to raise the pH of water containing the composition of this invention to the point of calcium carbonate precipitation. Since pH creep (increasing pH with time) is very common in swimming pools, these results indicate that addition of the composition of this invention will result in less maintenance for the pool owner or operator. The test results possibly suggest a synergistic relationship of the borates with bicarbonate alkalinity.

EXAMPLE 2

Dissolution Rate of Partially Neutralized Cyanuric Acid Salts

Samples of cyanuric acid sodium salts (0.2 g) were placed in 3 L of water and stirred with a mechanical stirrer at 200 rpm at room temperature. The time until complete dissolution was observed was recorded, as well as the pH of the final solution. Results are presented in Table II.

TABLE II

| pH | dissolution time (min.' sec.") |
|---|---|
| 7.6 | 17' 01" |
| 7.56 | 08' 54" |
| 7.5 | 10' 30" |
| 7.5 | 18' 30" |
| 7.44 | 24' 30" |
| 7.35 | 23' 08" |
| 7.27 | 09' 12" |
| 7.15 | 06' 24" |
| 7.03 | 08' 06" |
| 6.83 | 09' 54" |
| 6.78 | 05' 30" |
| 6.68 | 03' 40" |
| 6.60 | 05' 08" |
| 6.53 | 06' 01" |
| 4.66* | 36' 02" |

*cyanuric acid, 98%

The data demonstrate, surprisingly, that high-pH cyanurate salts, whose acidic groups are more completely neutralized, generally have longer dissolution times than lower-pH salts. Cyanuric acid itself, which has the lowest pH, has an extremely long dissolution time.

The invention claimed is:

1. A solid composition comprising:
   (a) a sodium or potassium salt of cyanuric acid having a pH from 6 to 7.2; and
   (b) a tetraborate salt and boric acid in amounts sufficient to produce a pH from 7 to 8.

2. The composition of claim 1 further comprising from 92% to 97% sodium chloride or potassium chloride.

3. The composition of claim 1 in which boric acid and sodium tetraborate pentahydrate are present in a ratio from 1.5:1 to 4:1.

4. The composition of claim 3 further comprising a metal chelating agent.

5. The composition of claim 4 in which the metal chelating agent is EDTA.

6. The composition of claim 2 in which a sodium or potassium salt of cyanuric acid is present in an amount from 1% to 3.5%.

7. The composition of claim 6 in which a sodium salt of cyanuric acid is present in an amount from 1% to 3.5%, and has a pH from 6 to 7.2.

8. The composition of claim 7 comprising from 92% to 97% sodium chloride.

9. A method for providing chlorinated water for recreational purposes by adding solids comprising:
   (a) a sodium or potassium salt of cyanuric acid having a pH from 6 to 7.2;
   (b) a tetraborate salt and boric acid in amounts sufficient to produce a pH from 7 to 8; and
   (c) sodium chloride or potassium chloride;

to a body of recreational water equipped with a chlorine generator, followed by electrolysis of the treated water to produce chlorine.

10. The method of claim 9 in which sodium chloride or potassium chloride comprises 92% to 97% of the solids; boric acid and sodium tetraborate pentahydrate are present in the solids in a ratio from 1.5:1 to 4:1; and a sodium or potassium salt of cyanuric acid comprises from 1% to 3.5% of the solids.

11. The composition of claim 6 in which a sodium salt of cyanuric acid is present in an amount from 1% to 3.5%, and contains from 7% to 10% sodium.

12. The composition of claim 6 in which a potassium salt of cyanuric acid is present in an amount from 1% to 3.5%, and contains from 10.9% to 15.5% potassium.

13. The method of claim 10 in which sodium chloride comprise 92% to 97% of the solids; a sodium salt of cyanuric acid comprises from 1% to 3.5% of the solids; and the sodium salt of cyanuric acid contains from 7% to 10% sodium.

14. The method of claim 13 further comprising a metal chelating agent.

15. The method of claim 14 in which the metal chelating agent is EDTA.

* * * * *